US012274533B2

(12) United States Patent
Eckert et al.

(10) Patent No.: US 12,274,533 B2
(45) Date of Patent: Apr. 15, 2025

(54) PUTATIVE ENERGY FIELD ANALYSIS USING NON-THERMAL PLASMA ARRAY

(71) Applicant: ChiScan Holdings LLC

(72) Inventors: Bradley N. Eckert, Chandler, AZ (US); Bryon K. Eckert, Chandler, AZ (US); Huan Truong, Chandler, AZ (US)

(73) Assignee: Iolera Holdings Pte. Ltd., Parkview Square (SG)

( * ) Notice: Subject to any disclaimer, the term of this patent is extended or adjusted under 35 U.S.C. 154(b) by 517 days.

(21) Appl. No.: 17/609,333

(22) PCT Filed: May 6, 2020

(86) PCT No.: PCT/US2020/031725
§ 371 (c)(1),
(2) Date: Nov. 5, 2021

(87) PCT Pub. No.: WO2020/227443
PCT Pub. Date: Nov. 12, 2020

(65) Prior Publication Data
US 2022/0151498 A1 May 19, 2022

Related U.S. Application Data

(60) Provisional application No. 62/843,978, filed on May 6, 2019.

(51) Int. Cl.
*A61B 5/0205* (2006.01)
*A61B 5/0245* (2006.01)
*A61B 5/053* (2021.01)

(52) U.S. Cl.
CPC .......... *A61B 5/0205* (2013.01); *A61B 5/0245* (2013.01); *A61B 5/053* (2013.01)

(58) Field of Classification Search
CPC ..... A61B 5/0205; A61B 5/024; A61B 5/0245; A61B 5/05; A61B 5/053
See application file for complete search history.

(56) References Cited

U.S. PATENT DOCUMENTS 4,357,709 A 11/1982 Butler et al.
5,115,168 A 5/1992 Shoda et al.
(Continued)

OTHER PUBLICATIONS

Arata Y., et al., "Contribution of Higher Harmonic Resonance on the Production of ECR Mirror Plasma by 60 GHz Gyrotron," Japanese Journal of Applied Physics, Feb. 1989, vol. 28(2), pp. 234-239.
Ibrahim M., et al., "Performance Analysis of Fast Fourier Transform on Field Programmable Gate Arrays and Graphic Cards," 2016, 5 pages.
International Search Report and Written Opinion issued in International Application No. PCTUS2020031725, mailed on Jul. 22, 2020, 6 pages.
(Continued)

*Primary Examiner* — Michael T Rozanski
(74) *Attorney, Agent, or Firm* — Messner Reeves LLP

(57) ABSTRACT

A device for detecting and analyzing vital fields includes: a dielectric barrier discharge array fabricated on a thin substrate with low dielectric loss; an air permeable sheet for electrical insulation from the skin; a transformer for generating sufficient AC voltage to cause air breakdown in the array; a signal transformer and bypass capacitor for isolating the radio frequency current from the plasma discharge; circuitry for amplification and narrow-band spectrum analysis of the plasma discharge current. The amplified signal from the plasma discharge current is gated to include only signal from the part of the drive waveform where plasma discharge predominantly occurs. Frequency converters reduce the complexity of narrow-band spectrum analysis; spectrum analysis is done by Fast Fourier Transform analysis of the frequency converter outputs. The different FFT results are compared and analyzed to aid the user with the correct array placement on the body, and the detection of medical conditions.

10 Claims, 3 Drawing Sheets

(56) References Cited

U.S. PATENT DOCUMENTS

| | | | |
|---|---|---|---|
| 5,130,003 | A | 7/1992 | Conrad |
| 5,363,054 | A | 11/1994 | Bekefi |
| 5,705,931 | A | 1/1998 | Klick |
| 5,909,086 | A | 6/1999 | Kim et al. |
| 6,347,238 | B1 | 2/2002 | Levengood et al. |
| 6,713,965 | B2 | 3/2004 | Jang et al. |
| 7,564,419 | B1 | 7/2009 | Patel |
| 8,460,283 | B1 | 6/2013 | Laroussi et al. |
| 2004/0135590 | A1 | 7/2004 | Quon |
| 2005/0116871 | A1 | 6/2005 | Moheb et al. |
| 2008/0097183 | A1 | 4/2008 | Monro |
| 2009/0292196 | A1 | 11/2009 | Eckert et al. |
| 2010/0296977 | A1 | 11/2010 | Hancock |
| 2011/0109519 | A1 | 5/2011 | Quan et al. |
| 2011/0118556 | A1 | 5/2011 | Siegel et al. |
| 2012/0156093 | A1 | 6/2012 | Kitano |
| 2012/0309328 | A1 | 12/2012 | Morrison et al. |
| 2013/0253302 | A1 | 9/2013 | Eckert et al. |
| 2014/0088433 | A1 | 3/2014 | Shan |
| 2014/0263202 | A1 | 9/2014 | Partridge |
| 2014/0309522 | A1 | 10/2014 | Fullerton et al. |
| 2014/0319382 | A1 | 10/2014 | Hancock et al. |
| 2015/0056107 | A1 | 2/2015 | Hancock |
| 2016/0065256 | A1 | 3/2016 | Yun et al. |
| 2016/0317061 | A1 | 11/2016 | Ostadrahimi et al. |
| 2016/0337986 | A1 | 11/2016 | Broda et al. |
| 2016/0372310 | A1 | 12/2016 | Chung et al. |
| 2017/0367613 | A1 | 12/2017 | Eckert et al. |
| 2021/0068896 | A1 | 3/2021 | Eckert et al. |

OTHER PUBLICATIONS

Jackson G.L., et al., "Second Harmonic Electron Cyclotron Pre-Ionization in the DIII-D Tokamak," Nuclear Fusion, Mar. 19, 2007, vol. 47, pp. 257-263.

Kamoda H., et al., "Millimeter-Wave Beam Former Using Liquid Crystal," 34th European Microwave Conference, 2004, pp. 1141-1144.

Nie Q Y., et al., "A Two-Dimensional Cold Atmospheric Plasma Jet Array for Uniform Treatment of Large-Area Surfaces for Plasma Medicine," New Journal of Physics, 2009, vol. 11, 15 pages.

Rubinski D., "Incremental Encoder Ouput Signal Overview," Wayback Machine Document, 2015, 1 page.

Sathasivam S., et al., "ASIC Implementation of High throughout FFT Processor for Scientific Applications," 2016, 5 pages.

Schmuck S., et al., "Electron Cyclotron Emission Spectra in X- and O-Mode Polarisation at JET: Martin-Puplett Interferometer, Absolute Calibration, Revised Uncertainties, Inboard/Outboard Temperature Profile, and Wall Properties," Review of Scientific Instruments, 2016, vol. 87(9), pp. 1-25.

Udintsev., V.S., et al., "New ECE Diagnostics for the TEXTOR-94 Tokamak," Review of Scientific Instruments, Jan. 3, 2001, vol. 72 (1), pp. 359-362.

Wiltse J.C., "History of Millimeter and Submillimeter Waves," IEEE Transactions on Microwave Theory and Techniques, Sep. 9, 1984, vol. 32 (9), 10 pages.

Yang Z., et al., "Vital Sign and Sleep Monitoring Using Millimeter Wave", ACM Transactions on Sensor Networks, Apr. 30, 2017, Retrieved from the Internet: https://dl.acm.org/doi/pdf/10.1145/3051124https://dl.acm.org/doi/pdf/10.1145/3051124./url:>.

PUTATIVE ENERGY FIELD ANALYSIS USING NON-THERMAL PLASMA ARRAY

CROSS-REFERENCE TO RELATED APPLICATIONS

This application is a U.S. National Stage of PCT Application No. PCT/US2020/031725 filed on May 6, 2020 which claims the benefit of priority from U.S. Provisional Patent Application Ser. No. 62/843,978, filed under the same title on May 6, 2019, and incorporated fully herein by reference.

FIELD OF INVENTION

This invention relates to pattern analysis. In particular it relates to methods and devices for detecting and analyzing energy fields emitted by organisms.

BACKGROUND

All live organisms emit energy fields, referred to herein as vital fields, which are characterized by the organic processes that produce or modify them. There is a significant amount of skepticism surrounding vital fields because no known scientific instruments can detect them. The inability to detect, measure, and describe the energy in a vital field is a problem that inhibits human understanding of biological interactions with the environment.

A wave in an energy field is considered to be composed of electric, magnetic, gravitational and temporal components. The electric, magnetic, and gravitational components are orthogonal to each other. In an electromagnetic wave, the gravitational and temporal components have a static value, and the electric and magnetic components vary inversely. In this context, a static temporal component equates to time moving forward at a constant rate. In contrast, a vital wave is theorized to contain static electric and magnetic components and dynamic temporal and gravitational components. Such a wave is essentially a longitudinal or compression wave in the space-time fabric, but is often referred to as a torsion wave. Because vital waves do not have a dynamic magnetic component, they do not induce a current in a conductor. Most known devices rely on such induction and are therefore unable to reliably detect the presence of vital waves or measure or describe them scientifically.

Kirlian photography, discovered in the early 20th century, can be considered one of the earliest means of analyzing vital fields. Kirlian photography works by driving a photographic plate at high voltage, with a biological specimen resting on the plate. The resulting image left on the film is consistent with the corona discharge pattern of the specimen. Live specimens tend to show a shimmering coronal effect, whereas dead specimens and inanimate objects exhibit a more uniform pattern. The difference is attributed to the live specimen having at least one vital field. It should be noted, however, that Kirlian photography as an indicator of vital fields has been met with skepticism, with the results explained away as errors in the experimental process.

Plasmas are a fourth possible state of matter, the others being solid, liquid, and gas. Plasmas are formed when a gas is subjected to high stresses that create a mixture of neutral atoms, positively charged atomic and molecular ions, and freed electrons. Non-thermal plasmas occur when the electrons are much more energetic than the neutral or positively charged particles. The application of non-thermal plasma in medicine has recently been a fruitful field of research. The beneficial health effects of non-thermal plasma applications in living organisms are often attributed to reactive oxygen or nitrogen species. Closer investigation of the health effects imparted by an array of micro-plasmas placed near the skin shows energetic effects that are not explained by conventional science. If these energetic effects can be electronically analyzed in real time, the information can be used to provide feedback to the user to show the optimum application of plasma to the body, the progress of healing, and the amount of pain.

SUMMARY

The present device is a putative energy field analyzer that detects energy fields converted to electromagnetic energy by a plasma emitter array. The plasma emitter array can be a dielectric barrier discharge array fabricated on a thin substrate with low dielectric loss. This can be FR-4, PEEK, a cyclic olefin fiberglass laminate or other similar low loss material. The oxygen plasma will erode the polymer over time, but the array lifetime can be extended with a thin film of oxide, typically aluminum oxide deposited by atomic layer deposition.

An applied AC voltage causes breakdown of the surrounding air in the sub-nanosecond range. The array is typically covered by an air permeable, electrically insulating sheet and placed next to the skin. The velocity of the plasma away from the electrodes is inversely proportional to the size of the plasma discharge. In the case of the micro-plasma, it is sufficiently high to cause relativistic effects. This converts the torsion waves of the vital field emanating from the body to electromagnetic waves that are conducted through the plasma array.

The array of plasma plumes provides a large number of mutually coupled areas of population inversion. This is caused by the collapsing non-linear magnetic field during the plasma discharge. The polar nature of the oxygen molecule causes a large number of hyperfine resonant frequencies from 53 GHz to 2.5 THz and beyond. At these frequencies, amplification by stimulated emission can take place.

Because each plasma plume discharges at a slightly different time, spontaneous emission from the array will manifest as broadband noise. However, a biological specimen will generate a large number of modulated carriers close to the hyperfine resonant frequencies of oxygen. These carriers are not detectable with normal millimeter-wave electronics, since there is no dynamic magnetic component in the torsion waves that comprise the vital energy field.

When the array is placed close to the skin, the plasma plumes convert this energy to electromagnetic waves that might be detected by extremely sensitive millimeter-wave electronics, but the cost is very high and this approach is not suited to a consumer device intended for broad usage. However, the conversion process between torsion wave vital energy and electromagnetic energy through plasma interaction is a non-linear process. This creates mixing products between the carriers, some of which can be analyzed in the VHF and UHF frequency ranges. To help reject radio signals, these signals are analyzed by narrow-band spectrum analysis.

DETAILED DESCRIPTION

Figure 1:
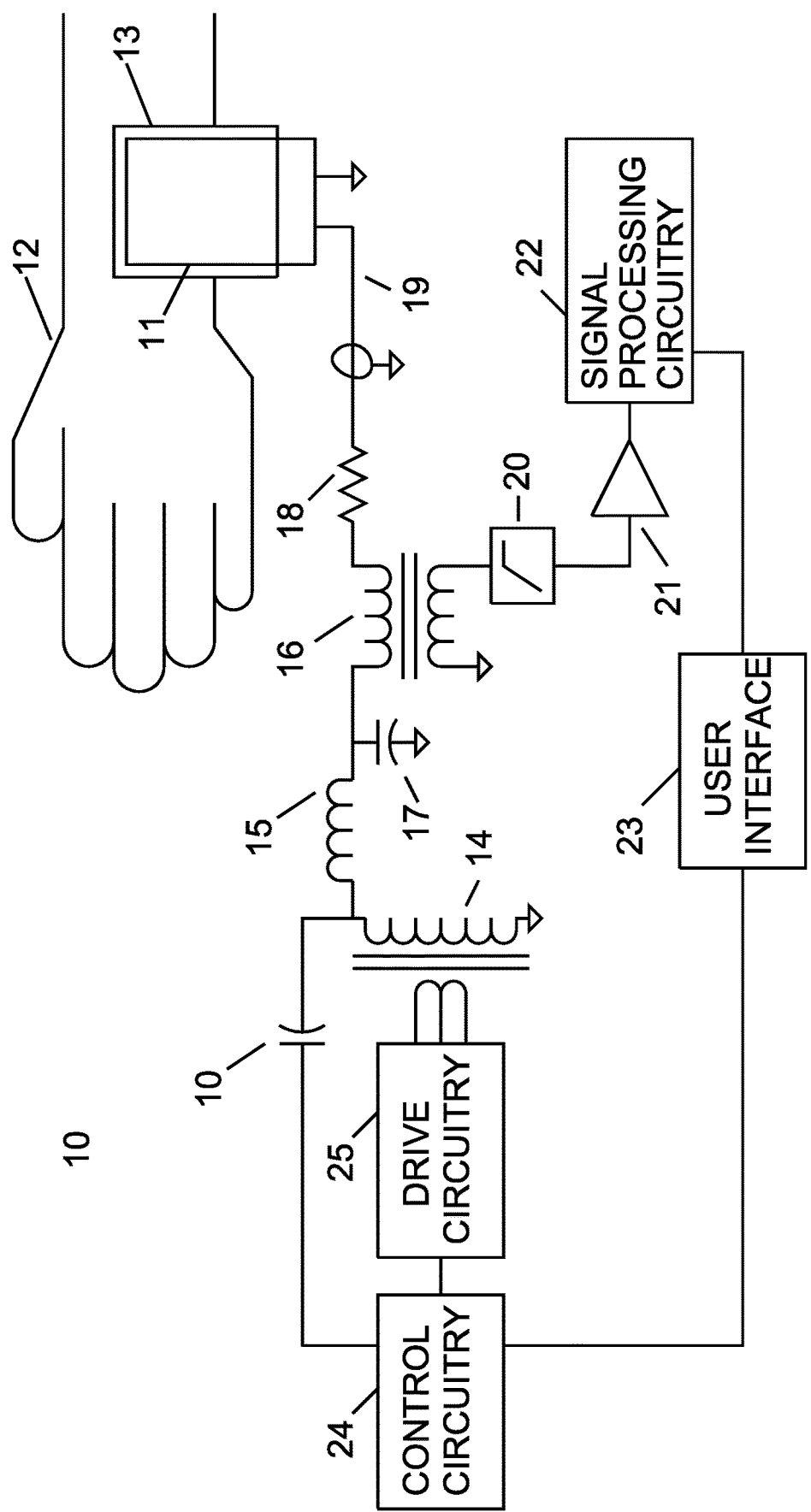
FIG. 1 is a schematic diagram of an example putative energy field analyzer in accordance with the disclosure.

FIG. 1 illustrates the presently described systems and an example method of use. The system 10 may generate an array of non-thermal plasma plumes for plasma medicine applications. An array 11 electrically insulated by an air-permeable sheet or pouch 13 may be placed next to the skin 12 of a living organism. The array 11 is driven by high voltage transformer 14, through high frequency filter inductor 15, signal transformer 16, resistor 18 and optional coaxial cable 19. A combination of bypass capacitor 17 and signal transformer 16 may be used to detect high frequency current from the array 11 under conditions of air discharge. Resistor 18 is used to reduce signal reflections to allow a flatter frequency response.

An output of signal transformer 16 is filtered by high pass filter 20 to remove the array drive frequency component, which may typically be a value between 50 kHz and 150 kHz. Because of the array capacitance, the amplitude of the reverse power decreases with increasing frequency. The electric current frequency range is typically 10 MHz to 840 MHz in the high-frequency array. Low Noise Amplifier 21 may be used to minimize the system noise floor. This is connected to signal processing circuitry 22 and user interface 23. In a preferred embodiment the plasma discharges only occur in a defined phase window of the driving waveform. The ratio between the plasma current noise floor and the system thermal noise floor is maximized by gating the signal with a defined duty cycle and phase offset.

The drive circuitry 25 provides a primary drive for high voltage transformer 14. The control circuitry 24 provides power control and fault protection in case of array failure. In an example embodiment, the resonant frequency of the transformer and array combination is measured by the controller in a calibration routine. This may allow a faster shutdown in case of array failure or detection of array contamination. An alternative embodiment may use a self-oscillating transformer primary drive.

In this configuration, a low inductance is needed to overcome the capacitance of the array in order to drive it at high frequency. Due to the relatively small number of turns in the transformer, which carry the induced magnetic flux, the flux density in the ferrite core will be high. A high flux density causes high power dissipation in the core. In some embodiments this may be mitigated by modulating the AC voltage to reduce the average power dissipation, for example at a duty cycle of 30%.

In one embodiment, the modulation frequency may typically be set between 10 Hz and 5 kHz. Modulation frequency-dependent energetic effects have been demonstrated in-vitro and in-vivo by numerous researchers in plasma medicine. In a preferred embodiment, the modulation dictates a relatively narrow analysis bandwidth of about 11 kHz. In a preferred embodiment, the signal processing circuitry 22, user interface 23 and control circuitry 24 are implemented in an ASIC.

Figure 2A:
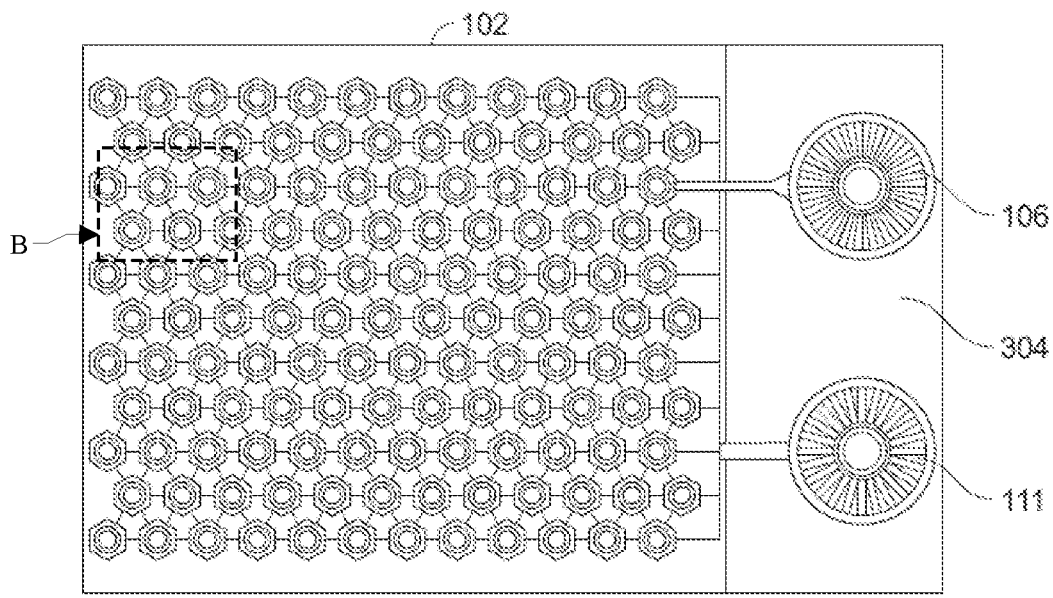
FIG. 2A is a top view of an example plasma emitter array in accordance with the disclosure.
Figure 2B:
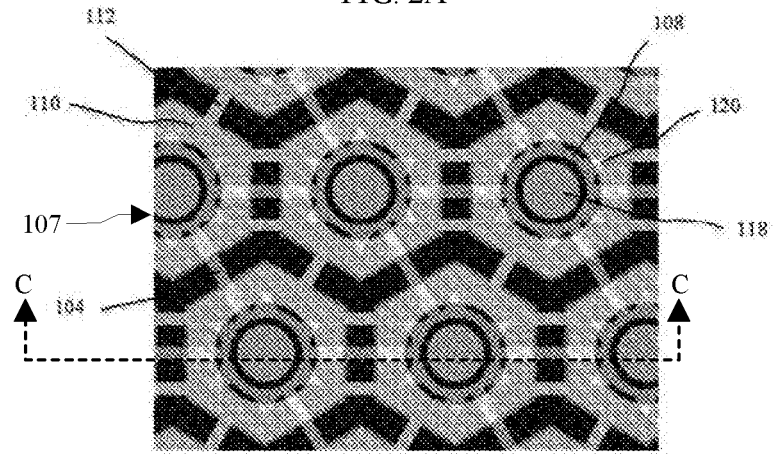
FIG. 2B is a close-up top view of the example plasma emitter array taken from Inset B of FIG. 2A.
Figure 2C:
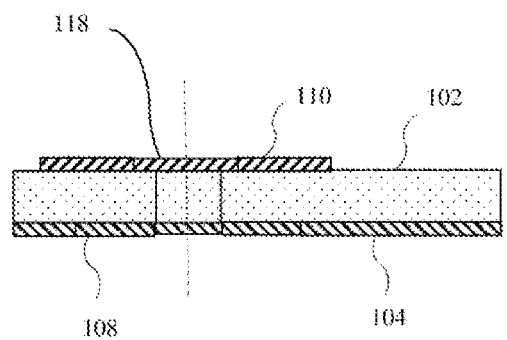
FIG. 2C is a cross-sectional side view of the plasma emitter array of FIG. 2A taken along line C-C of FIG. 2B.

FIGS. 2A-C illustrate a non-thermal plasma emitter array 100, such as the array 11 of FIG. 1. An array 100 comprises a plurality of non-thermal plasma emitters 107, disposed on a rigid or flexible substrate 102 having at least two opposing surfaces, referred to herein sometimes as a top and bottom for convenience. The emitters 107 are arranged such that when the array 100 is connected to a voltage source the emitters generate a plurality of corona discharges. The discharges generate ionized gas, which in turn creates reactive species including ozone and nitric oxide.

A plurality of through-holes 118 are made in the substrate 102. A through-hole 118 helps reduce the array capacitance and is a ventilation hole for a fluid to flow from a drive electrode 110 to a ground electrode 108. Such fluids include oxygen, helium, nitrogen, sulfur hexafluoride, carbon dioxide, air, and other gases. In the preferred embodiment, the fluid is air at ambient pressure, about 1 atmosphere. The oxygen in the air is ionized by the plasma generated by the emitters 107, creating ozone. The through-holes 118 are made by drilling, etching, cutting, laser cutting, punching, or other method. In certain embodiments a through-hole is lined with a structure that directs the fluid to each electrode such as a pipe, tube, channel, or the like. A through-hole 118 can be circular, rectangular, triangular, trapezoidal, hexagonal, or other shape.

A plurality of drive electrodes 110 is placed on the top of the substrate 102, with each drive electrode 110 centered over one through-hole 118 in the substrate 102. A plurality of ground electrodes 108 is placed on the bottom of the substrate 102, with each ground electrode 108 centered over one through-hole 118 in the substrate 102. The resulting structure of a through-hole, a ground electrode, and a drive electrode comprises a plasma emitter 107. Each drive electrode 110 and ground electrode 108 can be generally centered on a through-hole 118, as shown, but in certain embodiments it may be off-center. Each electrode's 110 shape is preferably symmetric around the through-hole 118, such as a hexagon, circle, triangle, rectangle, square, or other shape, but in certain embodiments can be asymmetric.

A conductive drive track 112 on the top of the substrate 102 is connected to at least one drive electrode 110. A conductive ground track 104 on the bottom of the substrate 102 is connected to at least one ground electrode 108. One or more drive tracks 112 may be used to interconnect as many drive electrodes 110 together as desired. Similarly, one or more ground tracks 104 may be used to interconnect as many ground electrodes 108 together as desired. Emitters 107 may be connected in series or in parallel, and preferably in parallel for a lower driving voltage.

A drive terminal 111 is connected to the drive track 112 and a ground terminal 106 is connected to the ground track 104. The drive electrodes 110 are interconnected and connected to a drive terminal 111. Similarly, the ground electrodes are interconnected and connected to a ground terminal 106. The resultant structure is much like a printed circuit board.

Figure 3:
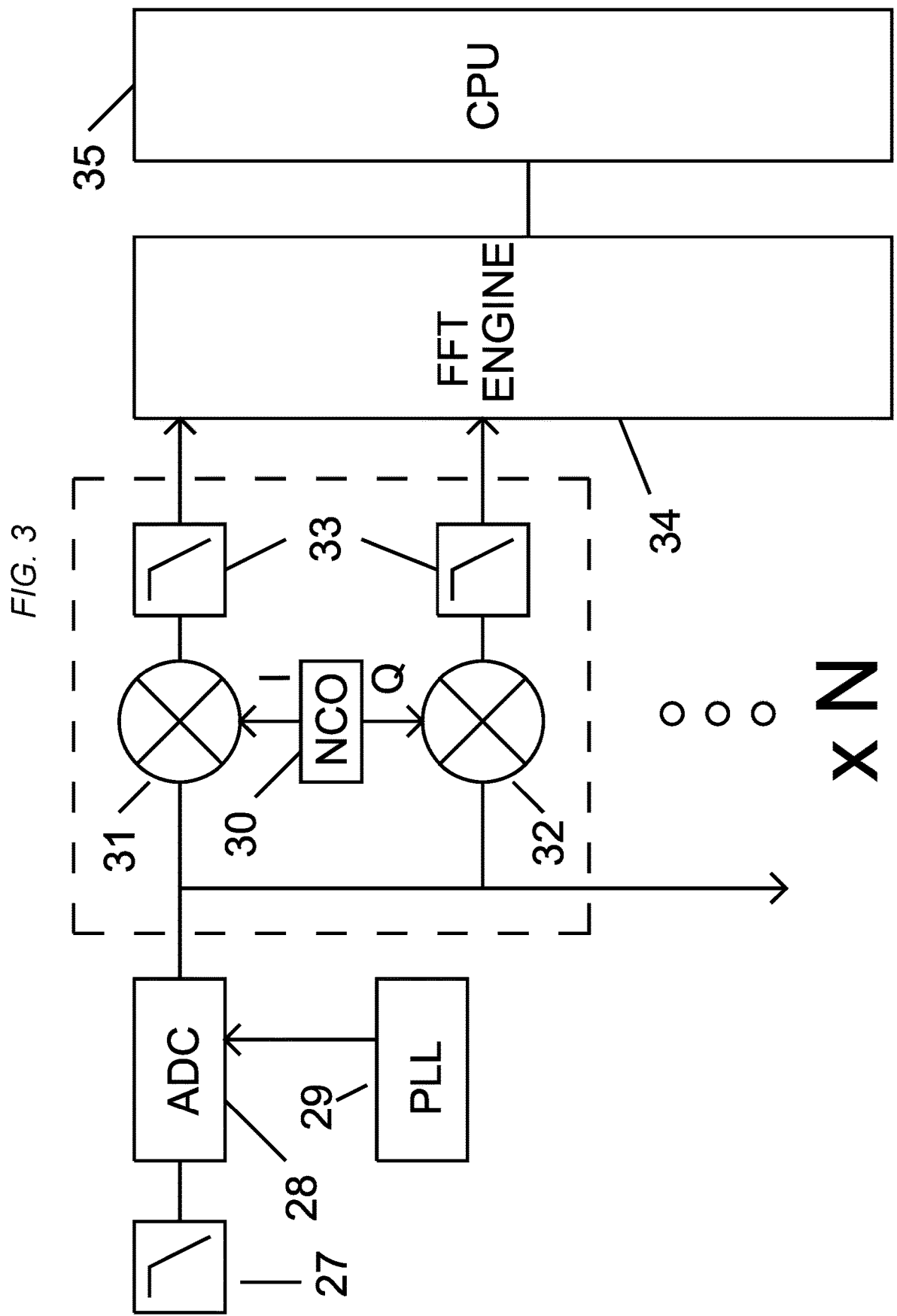
FIG. 3 is a block diagram of an example signal analysis system in accordance with the disclosure.

The substrate 102 is made of a dielectric material such as alumina, polycarbonate, polyimide, polyester, polytetrafluoroethylene-infused woven glass cloth, polypropylene, glass-reinforced epoxy laminate sheets, or the like. In certain embodiments a substrate has more than one layer, and the layers may be made of different materials. The substrate 102 is made of a rigid or a flexible material that can be made to conform to varying surface topography and shapes such as a rough surface, a textured surface, a smooth surface. The substrate can be two-dimensional, such as a square, curved, rectangular, round, or hexagonal. It can also be three-dimensional such as curved, cubic, tubular, or spherical. The substrate may also have a non-uniform shape or a non-symmetric shape. Substrates of rigid materials may be shaped to the desired conformation before or after the plasma emitters are made therein. Substrates of flexible materials are typically conformed to the desired shape after the array is manufactured. In a preferred embodiment, the substrate is made of thin FR-4. At a thickness of about 0.2 mm, the substrate made of FR-4 is somewhat flexible. As an alternative, the array can be fabricated from more flexible material such as polyimide film or PTFE infused fiberglass. An insulative layer 304 can be attached to the substrate 102, under the ground terminal 106 and driver terminal 111. The insulative layer 304 can be neoprene, polymer coating, Mylar®, Teflon®, or the like A drive electrode 110 is capacitively coupled to ground electrode 108 at a point or points where the ground electrode touches the drive electrode such that when a high-enough voltage is applied to a drive electrode 110, the surrounding fluid is ionized and a plasma is created, causing electrons to flow between the drive and ground electrode. It is desirable to have a sharp point where the plasma is generated, since this is used to help initiate the plasma. The sharp points may take any form, such as a sharp point, a blunt point, a spear point a radius, or the like. FIG. 3 illustrates an embodiment in which the ground electrode 108 is a star with six sharp points 120.

Using mass manufacturing techniques, the cost of making the arrays is small enough that the arrays can be considered consumable or disposable, simply thrown away or recycled after one or a few uses. Any polymer in the array is consumed by the oxygen plasma, in a process commonly known as ashing. This erosion process can be slowed by adding a thin layer of glass on top of the entire array. A sol-gel process can be used to deposit thick layer, on the order of about a 100 nm. A thinner crystalline layer of SiO2, Al2O3 or Y2O3 works too, and may be deposited by atomic layer deposition or plasma assisted atomic layer deposition, optionally after array burn-in for uniform plasma.

The signal analysis approach in the preferred embodiment of device 10 is shown in FIG. 3. In a typical embodiment, the high speed analog-to-digital converter (ADC) is implemented as a set of lower speed ADCs with a set of high speed sample-and-hold circuits with fixed phase offset between samples. A set of eight ADCs with Successive Approximation Array (SAR) architecture clocked at one eighth of the input clock rate will allow low power consumption and smaller die area relative to a higher performance solution.

For digital down-conversion, the ASIC digital logic is clocked in the UHF frequency range, such as 460 MHz in an example embodiment, using parallel multipliers to accommodate the ADC sample clock rate of 1840 MHz. The signal processing circuitry begins with a low pass analog filter 27 and high speed ADC 28. In order to minimize the probability of a clock harmonic blocking the desired signal, the ASIC clock input may be half of this frequency. Using a higher frequency is no advantage as the minimum clock rate is set by the individual SAR ADC clocks. The clock is preferably voltage tuned to mitigate the problem of desired signals being masked by spurious signals within the digital receiver. In a typical embodiment, the ASIC input clock frequency is approximately 230 MHz to support the parallel ADC interface. Phase-locked loop 29 multiplies the 230 MHz reference by a factor of 8 to clock an ADC at 1840 MHz. This supports analysis frequencies past 840 MHz.

In a digital down-converter, a Numerically Controlled Oscillator (NCO) 30 is also clocked at 1840 MHz. This drives an In-phase (I) multiplier 31 and Quadrature (Q) multiplier 32. A decimation occurs in low pass filters 33, typically implemented as a combination of cascaded integrator-comb (CIC) and finite impulse response (FIR) filters. Like an ADC, a high speed digital section may be implemented in one or more sections operated in parallel and clocked at a lower speed.

An ADC output may be connected to multiple digital down converters with a typical decimation factor of 65520, resulting in a final sample rate of 28 kHz. This process would yield an approximate upper bandwidth limit of about 10.5 kHz. In a preferred embodiment, frequency stability will be within 0.5 ppm, or 420 Hz at the highest frequency. This permits analysis within the highest frequency modulation side bands.

In a preferred embodiment, the outputs of filters 33 are analyzed in an 8192 point fast Fourier transform (FFT), preferably by dedicated FFT hardware 34 and by a CPU 35. The complex FFT outputs are added or subtracted to measure signals on a particular side of the NCO carrier. Since the plasma discharges only occur in a defined phase window of the driving waveform, much of the FFT input will be set to zero. The 8192 point FFT will require 280 ms to collect data.

In a preferred embodiment, the ASIC would typically be implemented in a 28 nm low power CMOS process. This would allow efficient power usage for the ADC and high speed digital circuitry, and permit 16 digital down converters within a total die size of about 2.5 mm square.

A relatively large number of digital down converters will permit flexible tuning and analysis, examining multiple side bands on a small number of carriers, or fewer side bands on a large number of carriers. In an alternative embodiment, a digital down converter uses a small decimation factor along with a large FFT to search for signals in a large frequency range. In this case, the ADC clock operates at three times the 10G ethernet reference clock, or 1933.594 MHz. This minimizes spurious signals as the ethernet clock is running during data capture.

The down converter output is transferred to a PC over a QSFP+ connection (40 Gbps) and analyzed by a GPU card with a large memory bandwidth, such as an Nvidia Tesla K-40. The GPU card runs a set of 12 FFTs of typical size $2^{25}$, combined with a window function for the FFT input and a sort function for the FFT output. This output may be used to find signals for various medical conditions or biological specimens.

Each torsion wave signal is expected to be modulated in the audio frequency range, so the maser inter-modulation signals are expected to contain mixing products of these modulation side bands. These signals may contain further mixing products with the plasma drive frequency and the plasma modulation frequency.

The outputs of each complex FFT will contain amplitude and phase information. The frequency, phase and amplitudes of the relevant FFT outputs may be analyzed to determine correlation to medical conditions, acupuncture meridians, pain and other parameters. Since a relatively small number of signal peaks are needed for data analysis, the data can be analyzed on the ASIC, or streamed over a USB or wireless connection.

In certain configurations, the plasma array may also act as a radio antenna. The system in the present disclosure includes a plasma feedback radio receiver device. When the plasma array is operated away from the body of a living organism the radio receiver device is able to collect data about the ambient environment. Collected results may be stored in a database connected to the system. Data from the database may be used to calibrate the plasma array for use with living organism. The stored results in the database may be used to differentiate ambient environmental radio signals from biofield signals generated by a living organism when the plasma array is operated next to the body.

Thus, in various non-limiting examples, embodiments, configurations, and/or implementations, the present disclosure provides a device for detecting and analyzing vital fields, the device including: a dielectric barrier discharge array fabricated on a thin substrate with low dielectric loss; an air permeable sheet for electrical insulation from the skin; a transformer for generating sufficient AC voltage to cause air breakdown in the array; a signal transformer and bypass capacitor for isolating the radio frequency current from the plasma discharge; circuitry for amplification and narrow-band spectrum analysis of the plasma discharge current. The amplified signal from the plasma discharge current is gated to include only signal from the part of the drive waveform where plasma discharge predominantly occurs. A multiplicity of frequency converters are used to reduce the complexity of narrow-band spectrum analysis; spectrum analysis is done by Fast Fourier Transform (FFT) analysis of the frequency converter outputs. The different FFT results are compared and analyzed to aid the user with the correct array placement on the body, and the detection of medical conditions.

The frequency converters can be implemented as analog circuitry. The amplified signal can be digitized by a high speed analog to digital converter; the frequency converters can be implemented as digital down converters and decimating filters. A small decimation digital down converter, or no down converter, is combined with a very long FFT to search for signals over a large range. The array is connected to the signal transformer through a length of coaxial cable. A series resistor can be added to reduce signal reflections on the coaxial cable.

The drive control for the high voltage transformer can be integrated into an Application Specific Integrated Circuit (ASIC), along with the narrow-band spectrum analysis circuitry and an associated Central Processing Unit (CPU) for real-time analysis. The ASIC is connected to a Bluetooth transceiver for the purpose of using a smart phone as a secondary user interface. The ASIC can consist of narrow-band spectrum analysis circuitry and an associated Central Processing Unit (CPU) for real-time analysis, and the plasma control is performed by a separate micro-controller; the plasma is modulated by turning it on and off at a set frequency and duty cycle. The plasma modulation frequency can be set to address the treatment of a specific physical condition. Reverse power generated by the plasma can be measured and used by the controller to find an optimum modulation frequency; the measured reverse power is used to provide feedback to the user. Radio signals in the VHF and UHF frequency ranges, generated by plasma interaction with the body, can be detected for the purpose of adjusting the modulation frequency.

While there has been illustrated and described what is at present considered to be the preferred embodiments of the present invention, it will be understood by those skilled in the art that various changes and modifications may be made and equivalents may be substituted for elements thereof without departing from the true scope of the invention. The embodiments of the invention described herein are not intended to be exhaustive or to limit the invention to precise forms disclosed. Rather, the embodiments selected for description have been chosen to enable one skilled in the art to practice the invention. Therefore, it is intended that this invention not be limited to the particular embodiments disclosed, but that the invention includes all embodiments falling within the scope of the appended claims.

What is claimed is:

1. A device for detecting and analyzing vital fields of an organism, the device comprising:
   a dielectric barrier discharge array fabricated on a thin substrate with low dielectric loss;
   an air permeable sheet for electrical insulation from skin of the organism;
   a transformer for generating sufficient AC voltage to cause air breakdown in the array;
   a signal transformer and a bypass capacitor for isolating a radio frequency current from a plasma discharge of the array; and
   circuitry for amplification and narrow-band spectrum analysis of the radio frequency current to produce an amplified signal of a plasma discharge current, wherein:
   the amplified signal from the plasma discharge current is gated based on a driving waveform to include only signal from the part of the drive waveform where plasma discharge predominantly occurs;
   a multiplicity of frequency converters are used to reduce the complexity of the narrow-band spectrum analysis;
   the spectrum analysis is done by Fast Fourier Transform (FFT) analysis of outputs of the multiplicity of frequency converters to produce a corresponding multiplicity of different FFT outputs; and
   the different FFT outputs are compared and analyzed to aid a user of the device with correct placement of the array on the body organism for detection of medical conditions correlated to the different FFT outputs.

2. The device of claim 1 wherein the frequency converters are implemented as analog circuitry.

3. The device of claim 1 wherein the amplified signal is digitized by a high speed analog to digital converter and the frequency converters are implemented as digital down converters and decimating filters.

4. The device of claim 1 wherein the array is connected to the signal transformer through a length of coaxial cable.

5. The device of claim 4 wherein a series resistor is added to reduce signal reflections on the coaxial cable.

6. The device of claim 1, further comprising:
   a high voltage transformer in electrical communication with and driving the array; and
   a drive control for the high voltage transformer, wherein the drive control for the high voltage transformer is integrated into an Application Specific Integrated Circuit (ASIC), along with the narrow-band spectrum analysis circuitry and an associated Central Processing Unit (CPU) for real-time analysis.

7. The device of claim 6 wherein the ASIC is connected to a transceiver for the purpose of using a smart phone as a secondary user interface.

8. The device of claim 6, further comprising a micro-controller that is separate from the ASIC and that is configured to perform plasma control.

9. The device of claim 1 wherein the plasma discharge of the array is modulated by turning the AC voltage to the array on and off at a plasma modulation frequency and a set duty cycle.

10. The device of claim 9 wherein radio signals in the VHF and UHF frequency ranges, generated by plasma interaction with the organism, are detected for the purpose of adjusting the plasma modulation frequency.

* * * * *